(12) United States Patent
Ellis-Fant (10) Patent No.: US 7,370,991 B1
(45) Date of Patent: May 13, 2008

(54) VOICE-CONTROLLED SURGICAL LIGHTING ASSEMBLY

(76) Inventor: Wanda J. Ellis-Fant, 6522 Pine Cone Cove, Memphis, TN (US) 38141

( * ) Notice: Subject to any disclaimer, the term of this patent is extended or adjusted under 35 U.S.C. 154(b) by 0 days.

(21) Appl. No.: 11/640,146

(22) Filed: Dec. 18, 2006

(51) Int. Cl.
*B60Q 1/24* (2006.01)
*F21S 1/24* (2006.01)
(52) U.S. Cl. .................. 362/233; 362/105; 362/253; 362/276; 362/804
(58) Field of Classification Search ............... 362/103, 362/105, 233, 253, 276, 802, 804; 607/88–94; 340/686.1, 686.2, 689
See application file for complete search history.

(56) References Cited

U.S. PATENT DOCUMENTS

| 3,830,230 | A | | 8/1974 | Chester |
| 4,631,644 | A | | 12/1986 | Dannhauer |
| 5,440,462 | A | | 8/1995 | Kim et al. |
| D362,080 | S | | 9/1995 | Lehrer et al. |
| 5,667,292 | A | | 9/1997 | Sabalvaro, Jr. |
| 5,757,339 | A | * | 5/1998 | Williams et al. ............... 345/8 |
| 5,844,656 | A | * | 12/1998 | Ronzani et al. ............. 351/158 |
| 6,348,859 | B1 | * | 2/2002 | Baker .......................... 340/479 |
| 6,554,444 | B2 | | 4/2003 | Shimada et al. |
| 6,955,444 | B2 | * | 10/2005 | Gupta ......................... 362/105 |
| 7,192,151 | B2 | * | 3/2007 | Clupper et al. ............. 362/105 |
| 7,303,303 | B1 | * | 12/2007 | Haynes et al. .............. 362/105 |

\* cited by examiner

*Primary Examiner*—John Anthony Ward (57) ABSTRACT

The assembly includes a strap adaptable to a variety of positions. Such a strap is placed directly about the user's head. A light-emitting source spaced from the strap includes a power supply source electrically coupled to the light-emitting assembly. Such a power supply source is rechargeable. A voice-activated mechanism for biasing the light-emitting source is defined from the strap so that the light-emitting assembly can be adapted along an x-axis, y-axis and z-axis. A motor assembly is directly and operably conjoined to the voice-activated mechanism and the light-emitting assembly. The voice-activated mechanism cooperates with the light-emitting source and the motor assembly during operating conditions. Such a voice operating mechanism is power-operated. The voice-activated mechanism is conveniently responsive to a user's voice commands in such a manner that the user can selectively operate the motor assembly and the light-emitting source from a remote location.

18 Claims, 12 Drawing Sheets

VOICE-CONTROLLED SURGICAL LIGHTING ASSEMBLY

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to lighting assemblies and, more particularly, to a lighting assembly for surgical use that is voice-operated.

2. Prior Art

For a light in an operation room of a hospital, a so-called astral lighting system has been used to illuminate the part of operation with high illuminance without casting shadows there.

An astral lighting system is constructed so that many lamps are embedded in a large dish-like base which is suspended from the ceiling of the operation room. Therefore, for its placement, a large room is needed and the ceiling of the operation room must be adequately high. Furthermore, because of its very heavy weight, not only the ceiling but also the whole operation room is required to be structurally strong. As a result, the construction cost of an operation room is high due to this lighting system.

Another problem of the astral lighting system is that it generates a large amount of heat. In a heart operation, however, the temperature of the patient's body must be kept low. In such case, a high-power cooling system must be provided to overcome the heat caused by the lighting system and lower the body temperature in a short time. This also has increased the construction cost of the operation room.

These drawbacks have spawned many attempts at head-mounted illuminating devices with the sole purpose of aiding patient visibility. Prior art embodiments include light sources which are separated from the headlamp to reduce the weight carried by the user. It is quite important, however, that the headlight be capable of positioning in virtually any desirable orientation as determined by the particular needs of the user. Specifically the light should be rotatable in planes perpendicular to, and coplanar with, the general sight plane of a user. Also, many prior art devices include manual switches which serve to hinder the sterility of a surgical environment as well as encumbering the user.

Accordingly, a need remains for a voice-controlled surgical lighting device in order to overcome the above-noted shortcomings. The present invention satisfies such a need by providing a voice-controlled surgical lighting device that is efficient, compact, adaptable, versatile, easily operated, and convenient. The voice-controlled surgical lighting device appeals to medical institutions such as hospitals and clinics as well as medical professionals and electricians or in any environment where head-mounted lighting is appropriate.

BRIEF SUMMARY OF THE INVENTION

In view of the foregoing background, it is therefore an object of the present invention to provide an assembly for voice-controlled surgical lighting. These and other objects, features, and advantages of the invention are provided by an assembly for providing light in a surgical setting controllable by voice commands.

The assembly includes a continuous and unitary strap adaptable to a variety of annular positions. Such a strap is advantageously and suitably sized and shaped for being placed directly about the user's head in such a manner that the strap remains above a line of sight of the user.

A light-emitting source distally spaced from the strap effectively includes a power supply source electrically coupled to the light-emitting assembly. Such a power supply source is conveniently rechargeable.

A voice-activated mechanism for biasing the light-emitting source between a variety of positions is distally defined from the strap so that the light-emitting assembly can be adapted along an x-axis, y-axis and a z-axis while a user's hands remain spaced from the lighting assembly.

A motor assembly is directly and operably conjoined to the voice-activated mechanism and the light-emitting assembly. The voice-activated mechanism cooperates with the light-emitting source and the motor assembly during operating conditions. Such a voice operating mechanism is power-operated. The voice-activated mechanism is conveniently responsive to a user's voice commands in such a manner that the user can advantageously and selectively operate the motor assembly and the light-emitting source from a remote location.

The voice-activated mechanism may include a microphone, a processor and an analog-to-digital converter electrically coupled to the microphone. Such a converter preferably receives an input signal in analog format based upon a user voice command and generates an output signal in digital format for effectively instructing the processor to perform a control logic algorithm responsive to the input signal. A memory may include software instructions for conveniently causing the light-emitting assembly to perform the steps of biasing the motor assembly and advantageously activating the light-emitting source between on and off positions respectively.

The motor assembly preferably includes a signal interface circuit that is electrically and directly coupled to the converter. A motor may be electrically coupled to the power supply source. An anchor bracket is monolithically formed with the strap and registered orthogonal thereto. Such an anchor bracket effectively has a hollow cavity housing the motor and directing an electrical lead line from the light-emitting source to the power supply source. A pair of actuating arms is directly and operably connected to the motor. A deformably non-resilient shaft preferably has opposed end portions directly conjoined to the actuating anchor bracket and monolithically formed with the actuating arms. Each of the actuating arms is selectively adaptable along a linear path such that the shaft becomes adapted along at least two opposing planes.

One of the end portions of the shaft may have an annular shape. The anchor bracket advantageously has an annular socket formed within a distal end portion thereof. The one end portion of the shaft is rotatably seated within the annular socket of the anchor bracket. Each of the actuating arms preferably includes a cylindrical housing provided with a centrally registered longitudinal axis traveling parallel to the anchor bracket. Such a housing has an axial bore formed therein.

A magnetically-actuated piston may be telescopically intercalated within the bore. A plurality of annular magnetic contacts is concentrically positioned about the bore and the piston. Such annular magnetic contacts may be selectively activated based upon the output signal effectively generated by the converter in such a manner that the piston linearly travels along the bore when exposed to oscillating magnetic fields emitted by the magnetic contacts.

The light-emitting assembly includes a housing preferably having an open distal end portion. A transparent lens may be conveniently seated within the distal end portion. A bulb is advantageously and centrally nested with the housing. Such a bulb is disposed proximally to the transparent lens for directing light rays outwardly and away from the housing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The assembly of this invention is referred to generally in FIGS. 1-13 by the reference numerals 10, 10' and 10" and is intended to provide a voice operated lighting assembly. It should be understood that the assembly 10, 10' and 10" may be used to operate many different types of electrical accessories and should not be limited in use only to lights.

Referring initially to FIGS. 1-4, the light-emitting assembly 10 includes a continuous and unitary strap 20 adaptable to a variety of annular positions. Such a strap 20 is advantageously and suitably sized and shaped for being placed directly about the user's head in such a manner that the strap 20 remains above a line of sight of the user. This is critical to the invention in that it allows for the hands free operation of the light-emitting assembly 10 without requiring constant adjustment by the user.

Referring again to FIGS. 1-4, a light-emitting source 21 distally spaced from the strap 20 effectively includes a power supply source 22 electrically coupled to the light-emitting assembly 10. Such a power supply source 22 is conveniently rechargeable. The placement of the power supply source 22 on the strap 20 is necessary to allow for proper balance of the assembly 10 when mounted on the head of the user.

Referring to FIGS. 1, 2, 7, 12 and 13, a voice-activated mechanism 30 for biasing the light-emitting source 21 between a variety of positions is distally defined from the strap 20 so that the light-emitting assembly 10 can be adapted along the x-axis, y-axis and z-axis while a user's hands remain spaced from the light-emitting assembly 10.

Referring to FIGS. 1-3, and 5, a motor assembly 40 is directly and operably conjoined, with no intervening elements, to the voice-activated mechanism 30 and the light-emitting assembly 10. The voice-activated mechanism 30 cooperates with the light-emitting source 21 and the motor assembly 40 during operating conditions. Such a voice-activated mechanism 30 is power-operated. The voice-activated mechanism 30 is conveniently responsive to a user's voice commands in such a manner that the user can advantageously and selectively operate the motor assembly 40 and the light-emitting source 21 from a remote location. This necessary feature allows the user to operate the assembly without requiring any manual interaction by the user, thus increasing efficiency and safety during surgical procedures or other tasks the user is performing as well as allowing the user to proceed in a timely fashion.

Figure 6:
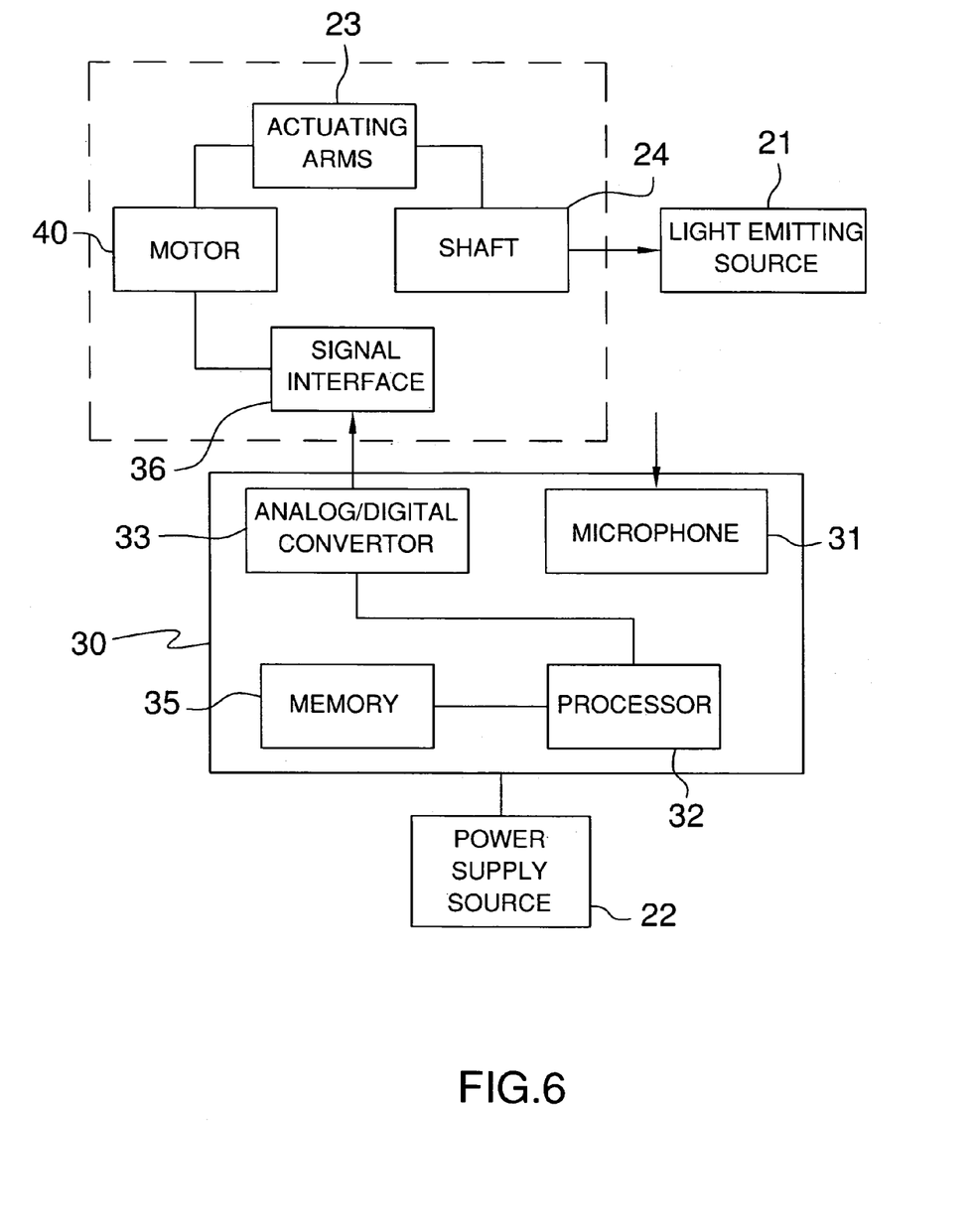
FIG. 6 is a schematic block diagram of the assembly shown in FIG. 1.
Figure 7:
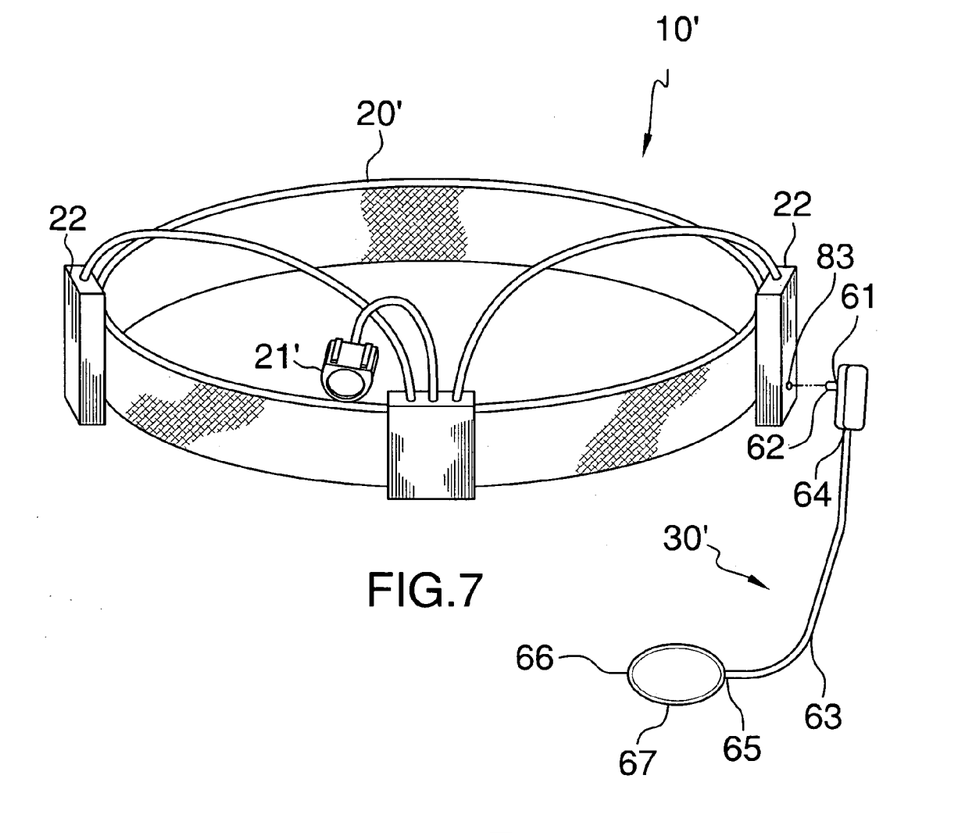
FIG. 7 is a perspective view of the assembly shown in FIG. 1 in an alternate embodiment.
Figure 8:
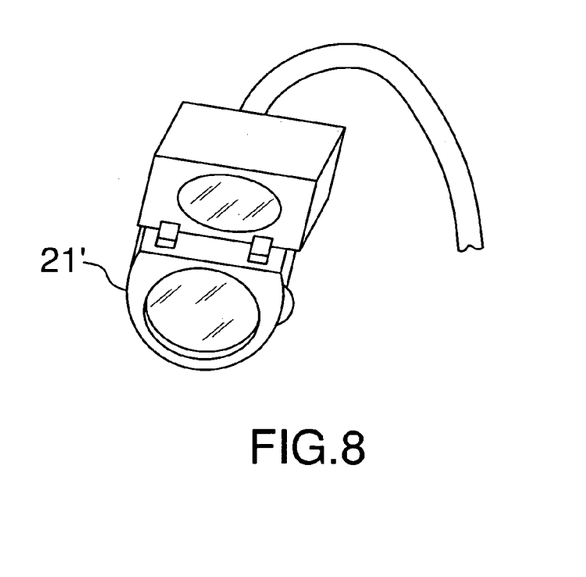
FIG. 8 is an expanded view of the light-emitting source shown in FIG. 7.
Figure 13:
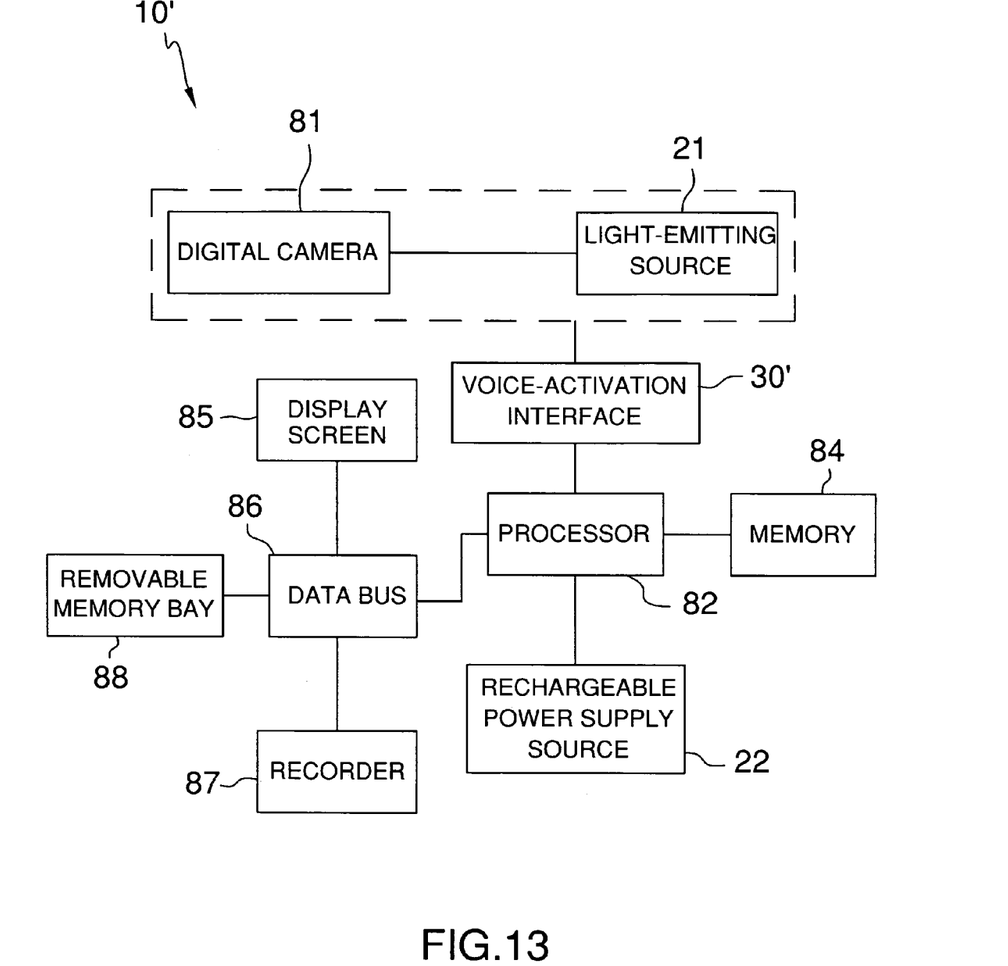
FIG. 13 is a schematic block diagram of the display shown in FIG. 9.

Referring to FIGS. 6, and 13, the voice-activated mechanism 30 includes a microphone 31, a processor 32 and an analog-to-digital converter 33 electrically coupled to the microphone 31. Such a converter 33 receives an input signal in analog format based upon a user voice command and generates an output signal in digital format for effectively instructing the processor 32 to perform a control logic algorithm responsive to the input signal. A memory 35 includes software instructions for conveniently causing the light-emitting assembly 10 to perform the steps of biasing the motor assembly 40 and advantageously activating the light-emitting source 21 between on and off positions respectively. Such a memory 35 may include various types such as ROM, RAM, or other applicable memory configurations to allow for the assembly to meet various requirements as mandated by the task to be performed.

Figure 1:
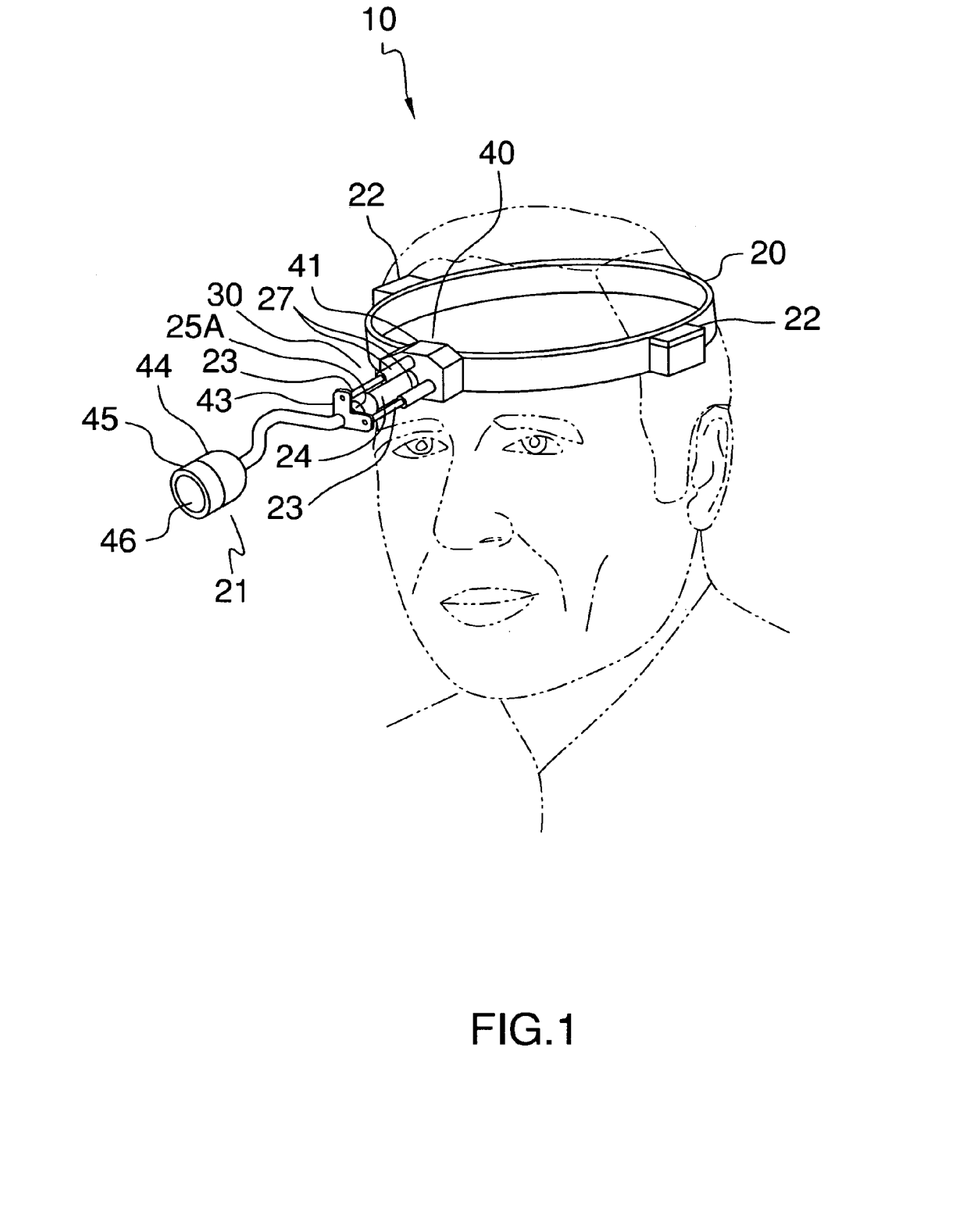
FIG. 1 is a perspective view showing a voice-controlled lighting assembly, in accordance with the present invention.
Figure 2:
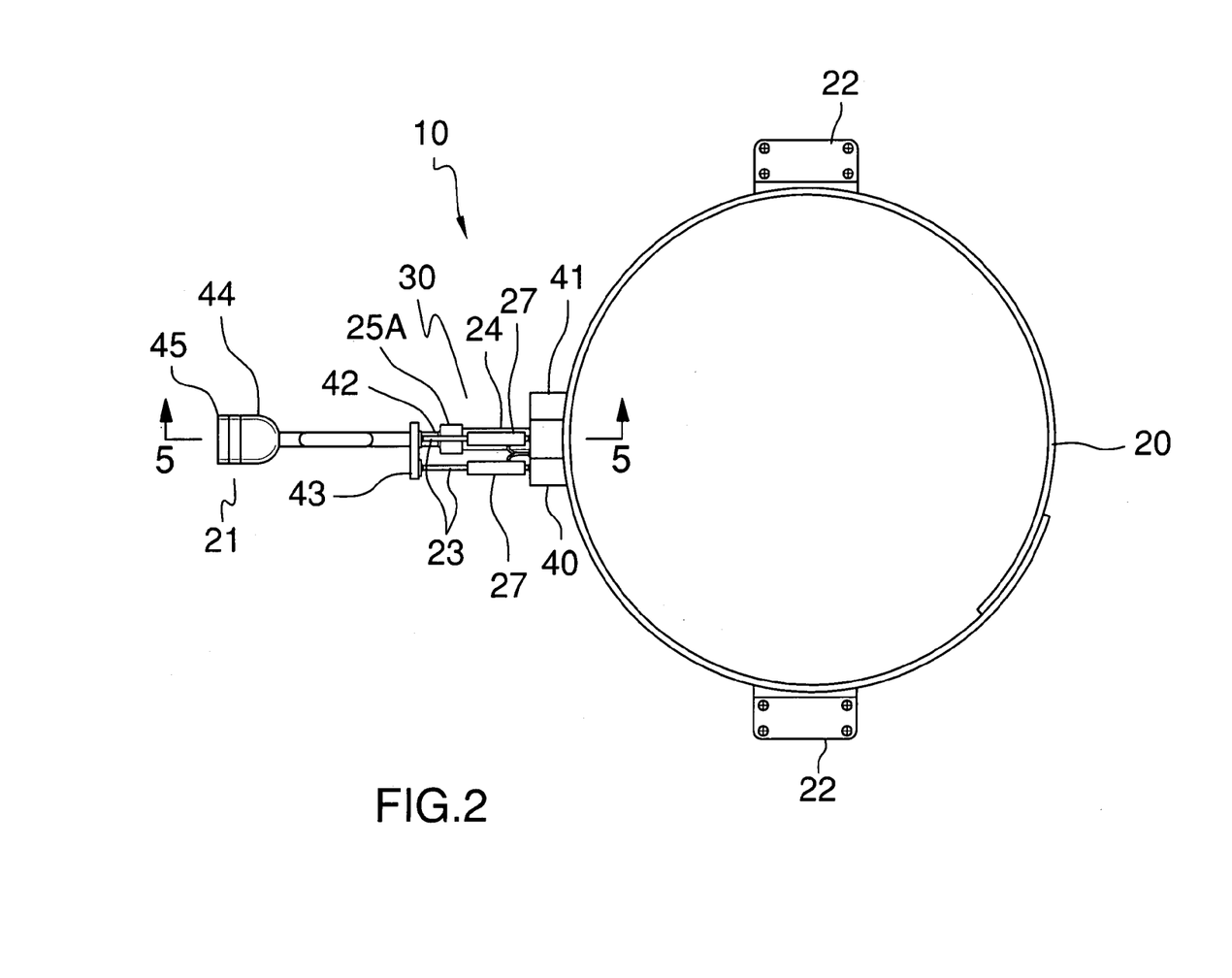
FIG. 2 is a top plan view of the assembly shown in FIG. 1.
Figure 3:
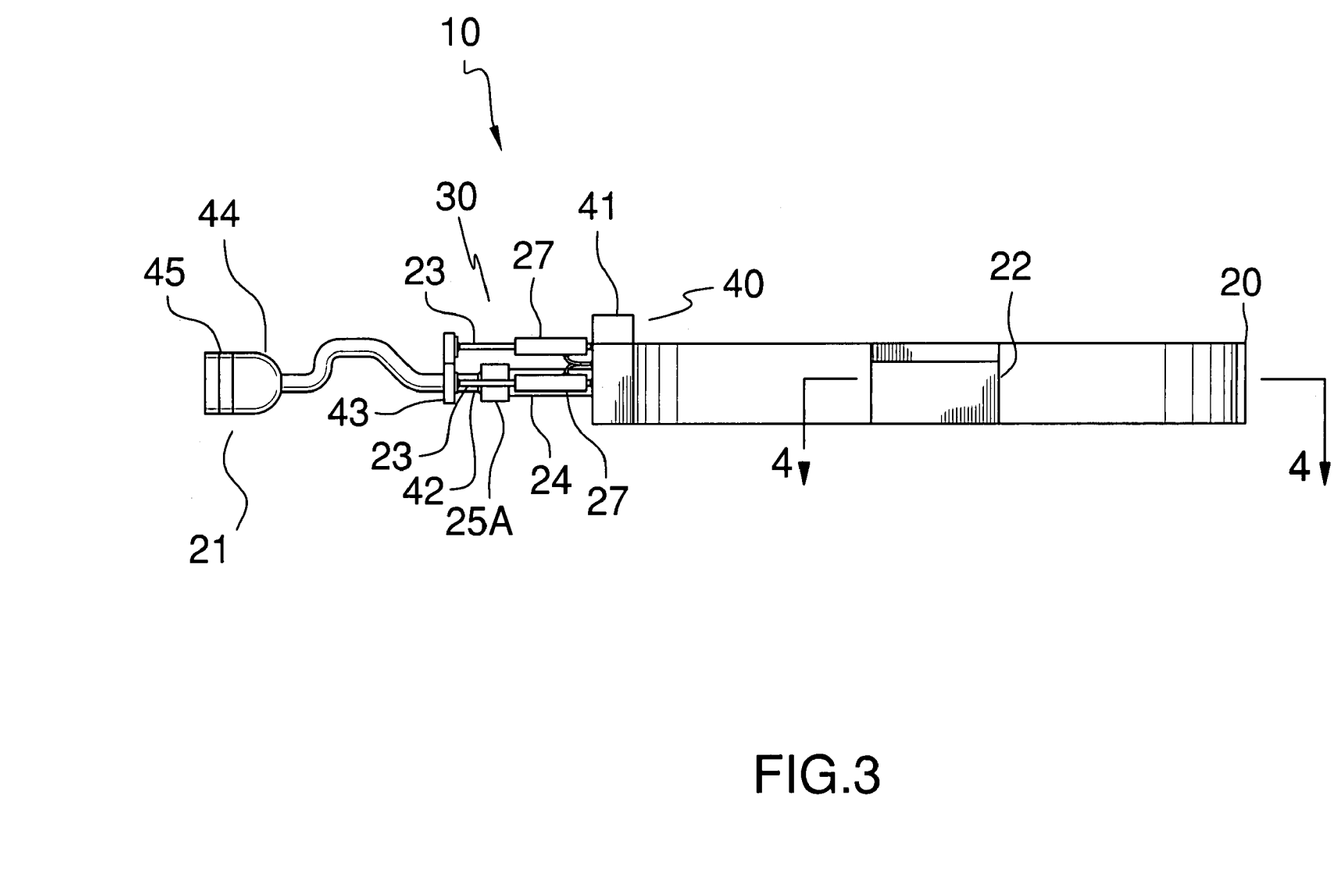
FIG. 3 is a side elevational view of the assembly shown in FIG. 1.
Figure 4:
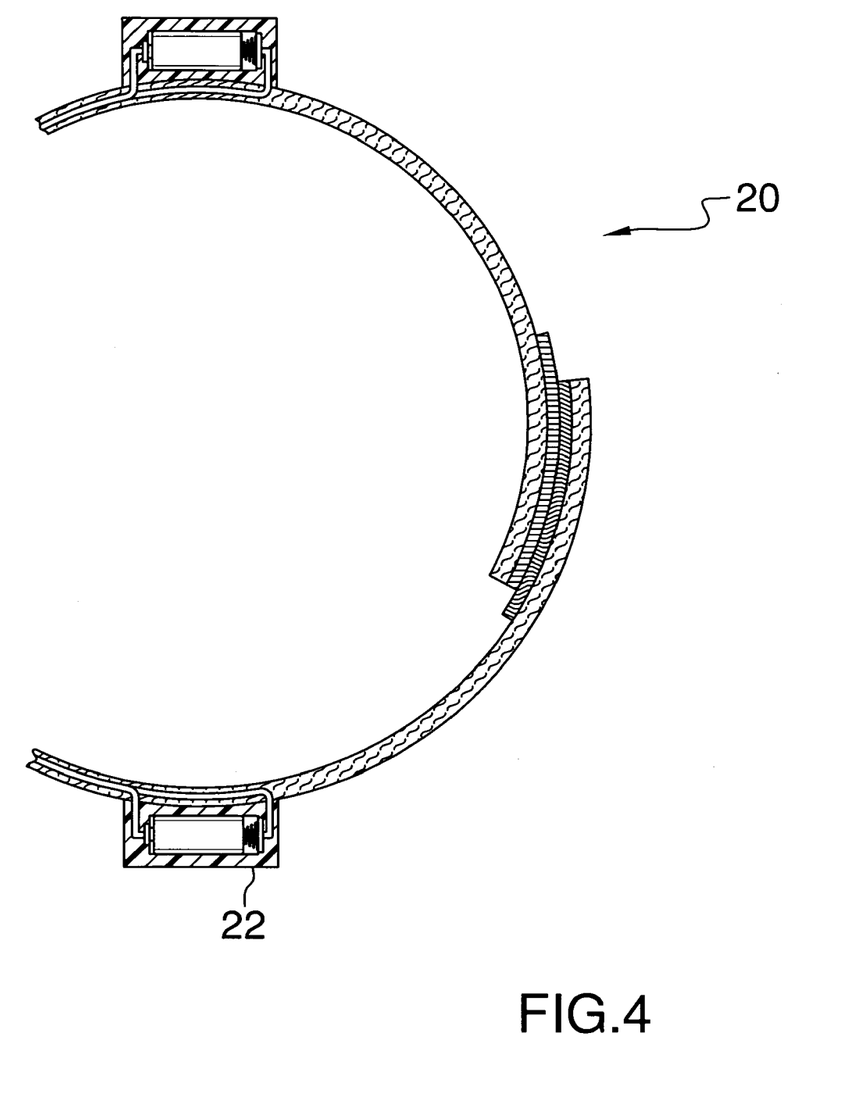
FIG. 4 is a partial cross-sectional view of the assembly shown in FIG. 3, taken along lines 4-4.
Figure 5:
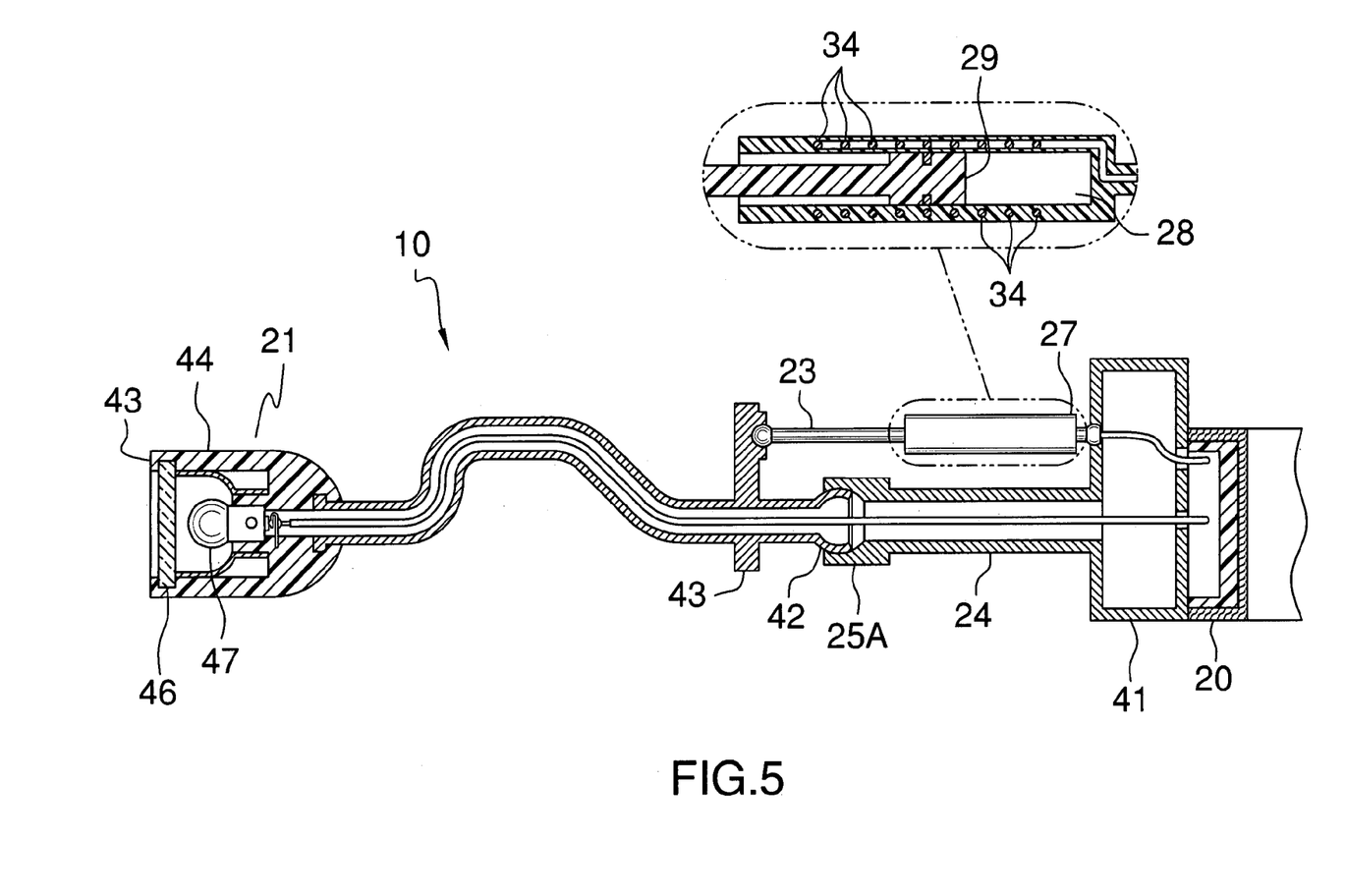
FIG. 5 is a partial cross-sectional view of the assembly shown in FIG. 2, taken along lines 5-5.

Referring to FIGS. 1, 5, and 6, the motor assembly 40 includes a signal interface circuit 36 that is electrically and directly coupled, with no intervening elements, to the converter 33. A motor 40 is electrically coupled to the power supply source 22. An anchor bracket 41 is monolithically formed with the strap 20 and registered orthogonal thereto. Such an anchor bracket 41 effectively has a hollow cavity 44 housing the motor 40 and directing an electrical lead line from the light-emitting source 21 to the power supply source 22.

A pair of actuating arms 23, is directly and operably connected, with no intervening elements, to the motor 40. A deformably non-resilient shaft 24 has opposed end portions 25 directly conjoined, with no intervening elements, to the actuating anchor bracket 41 and monolithically formed with the actuating arms 23. Each of the actuating arms 23 is selectively adaptable along a linear path such that the shaft 24 becomes adapted along at least two opposing planes. Referring to FIG. 5, one of the end portions 25A of the shaft 24 has an annular shape. The anchor bracket 41 advantageously has an annular socket 42 formed within a distal end portion 43 thereof. One end portion 25A of the shaft 24 is rotatably seated within the annular socket 42 of the anchor bracket 41. Each of the actuating arms 23 preferably includes a cylindrical housing 27 provided with a centrally registered longitudinal axis traveling parallel to the anchor bracket 41. Such a housing 27 has an axial bore 28 formed therein.

A magnetically-actuated piston 29 may be telescopically intercalated within the bore 28. A plurality of annular magnetic contacts 34 is concentrically positioned about the bore 28 and the piston 29. Such annular magnetic contacts 34 are selectively activated based upon the output signal effectively generated by the converter 33 in such a manner that the piston 29 linearly travels along the bore 28 when exposed to oscillating magnetic fields emitted by the magnetic contacts 34. This important aspect of the invention allows for the assembly 10 to be switched on and off by the user as a result of a signal output from the voice-activated mechanism 30.

Referring again to FIG. 5, the light-emitting assembly 10 includes a housing 44 having an open distal end portion 45. A transparent lens 46 may be conveniently seated within the distal end portion 45. A bulb 47 is advantageously and centrally nested with the housing 44. Such a bulb 47 is disposed proximally to the transparent lens 46 for directing light rays outwardly and away from the housing 44. This is essential as it allows the assembly 10, to effectively illuminate an area directly in front of the user to assist in performing a task or operation.

Referring to FIGS. 7, 8, 12 and 13, in an alternate embodiment, the lighting assembly 10' includes a voice-activation interface 30' operably attached to one of the power supply sources 22. Such a voice-activation interface 30' has a proximal 61 end including a protrusion 62 that is removably fitted to a corresponding receptacle 83 integrally formed in the associated power supply 22. A deformable wire 63 has a first end 64 that is directly attached to the proximal end 61 of the voice-activation interface 30' and a second end 65 that is directly attached to a distal end 66 of the voice-activation interface 30'. Such a distal end 66 terminates with a microphone 67 attached thereto.

Figure 9:
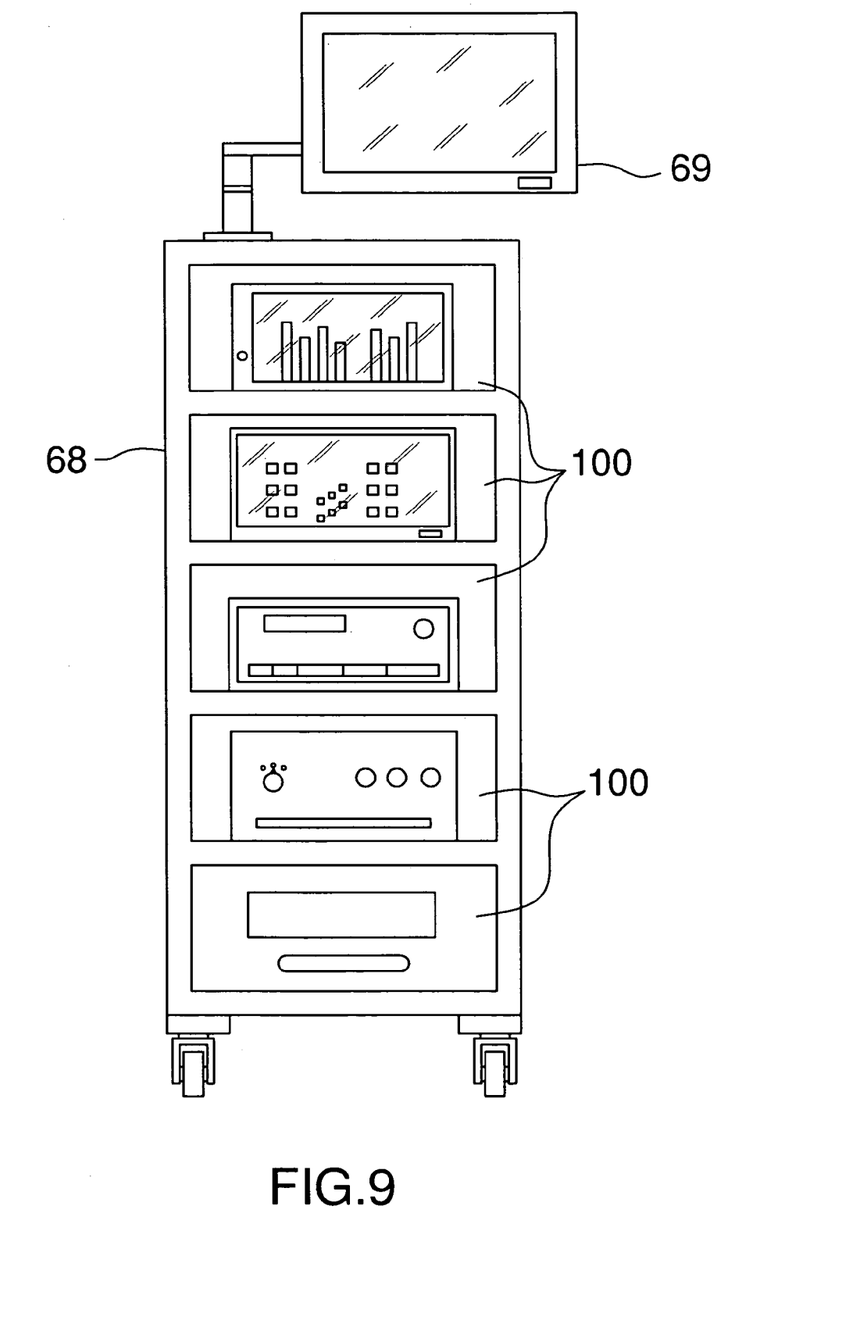
FIG. 9 is a front elevational view of the equipment display case and display screen.

Referring to FIG. 9, the assembly 10' further includes an equipment display case 68 and an associated display screen 69. Such a display case 68 effectively houses various types of electronic equipment 100 that are advantageously monitored and operated by a user during operating conditions. For example, a receiver, recorder and digital play back device may be employed by the present invention for storing real-time images and data over a restricted access network that can be accessed via a user name/password from remote locations. The enterprise software program may be uploaded on a network system at the hospital wherein a plurality of users may simultaneously access the real-time images and provide real-time feedback to a surgeon at the operating table. The data may be encrypted using 128-bit encryption technology conventionally found on web-based and DOS-based operating systems. Of course, streams of data may also be stored on non-volatile memory chips compatible with conventional PCs or laptops employing USB and Ethernet plug-ins interfaces, as well known to one skilled in the art. A web-based login page may also be employed by the present invention for allowing access to unrestricted images using a dedication communication link such as the telephony, DSL, T-1, Wi-Fi, or other well-known data communication links.

Figure 10:
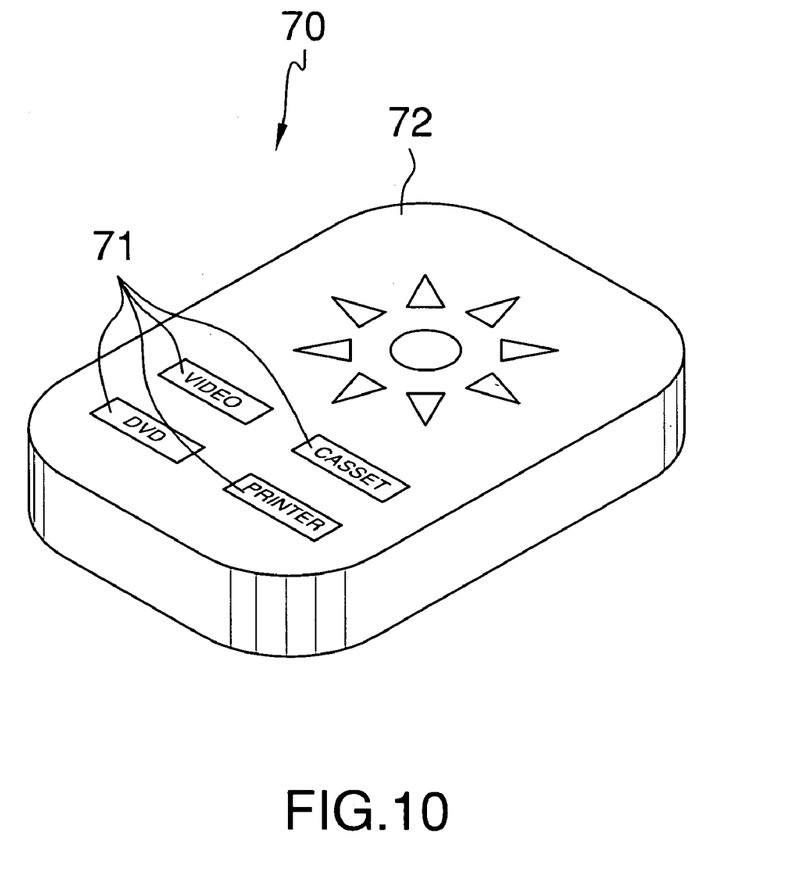
FIG. 10 is a perspective view of the remote control device.

Referring to FIG. 10, the assembly 10' further includes a remote control device 70. Such a remote control device 70 includes a plurality of switches 71 integrally housed within a top surface 72 thereof. Such switches 71 allow a user to remotely select and operate alternate electrical devices 100 housed within the display case 68 according to the desire of the user.

Figure 11:
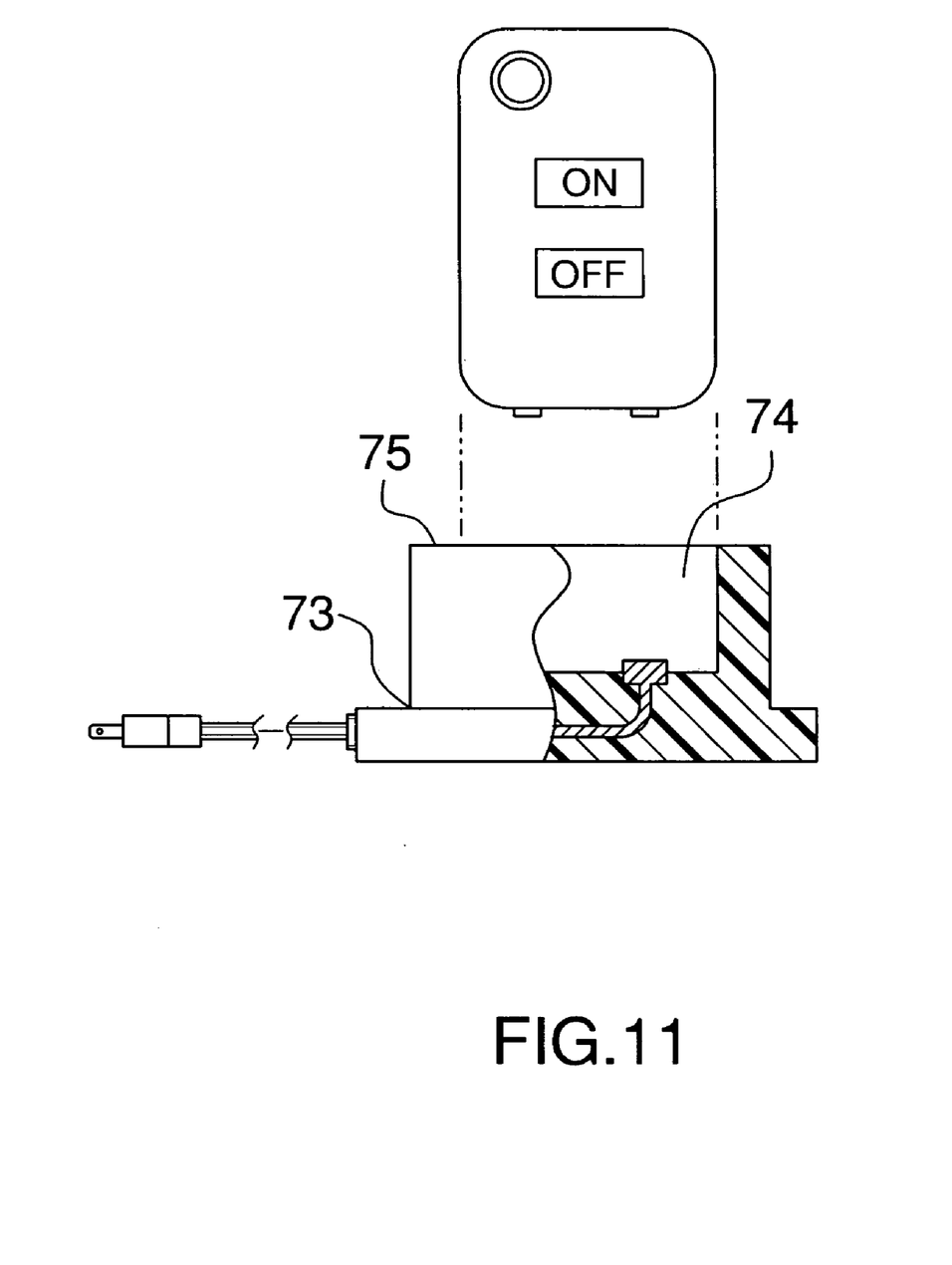
FIG. 11 is a side elevational partial cross-sectional view of the recharging station not shown in FIG. 7.

Referring to FIG. 11, the assembly 10' further includes a recharging station 73. Such a station 73 receives a power supply 22 in an associated docking bay 74 integrally formed in a top surface 75 thereof. The recharging station 73 houses the power supply 22 while recharging of the power supply 22 is performed. The power supply 22 is removable from the docking bay 74 so that a user may selectively change the power supply 22 as needed to operation conditions.

Figure 12:
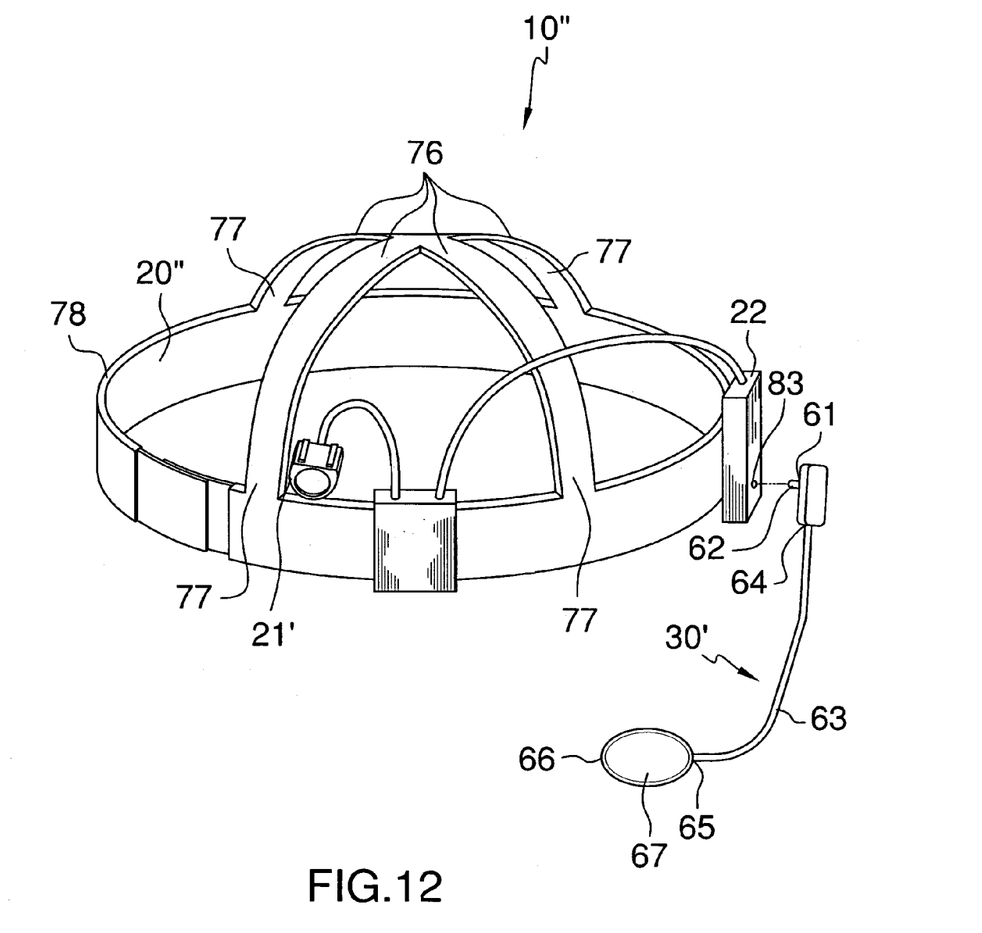
FIG. 12 is an alternate embodiment of the apparatus shown in FIG. 7 showing an arched strap system.

Referring to FIG. 12, in an alternate embodiment, the assembly 10" includes a plurality of straps 76 provided with opposed ends 77 directly connected to a top edge 78 of the unitary strap 20". Such straps 76 intersect orthogonally at a midway point of a longitudinal length thereof. The straps 76 intersect at a point located adjacent to a center point of a top outer surface of a user head and define a dome shape for maintaining continuous surface area contact along an apex of the user head and, thereby, minimizing undesirable movement during operating conditions.

Referring to FIG. 13 one skilled in the art will appreciate the non-obvious communication bridge developed between the various components of the present invention 10'. In particular, a digital camera 81 is electrically mated directly with a light emitting source 21, without the use of intervening elements. Such elements are also mechanically coupled to each other so that the operator may adjust a line of sight of the camera 81 while the light emitting source 21 remains stationary, and visa-versa. The voice-activation interface 30', described hereinabove, is electrically mated to a processor 82 (preferably a digital signal processor).

A memory 84 is electrically coupled to the processor 82. The memory 84 includes software instructions that cause the camera 81 and light emitting source 21 to automatically respond based upon a voice-command from the operator. Such a memory 84 preferably includes and executes a control logic algorithm that includes a plurality of operating steps for verifying a voice pitch level of the operator, sequencing the order of instructions and buffering the instructions to allow the operator to speak without directly interfering with operating procedures of the camera 81 and light emitting source 21. A display screen 85, data bus 86, recorder 87 and removable memory bay 88 are also included for providing real-time digital images over the enterprise software program while allowing the operator to manually transmit the images by using non-volatile memory such as a flash memory chip, for example.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A voice-activated lighting assembly positional about a user's head, said lighting assembly comprising:
   a continuous and unitary strap adaptable to a variety of annular positions, said strap being suitably sized and shaped for being placed directly about the user's head in such a manner that said strap remains above a line of sight of the user;
   a light-emitting source distally spaced from said strap;
   a power supply source electrically coupled to said light-emitting assembly;
   voice-activated means for biasing said light-emitting source between a variety of positions distally defined from said strap so that said light-emitting assembly can be adapted along an x-axis, y-axis and z-axis while a user's hands remain spaced from said lighting assembly; and
   a motor assembly directly and operably conjoined to said voice-activated means and said light-emitting assembly;
   wherein said voice-activated means cooperates with said light-emitting source and said motor assembly during operating conditions, said voice-activated means being responsive to a user's voice commands in such a manner that the user can selectively operate said motor assembly and said light-emitting source from a remote location.

2. The voice-activated lighting assembly of claim 1, wherein said voice-activated means comprises:
   a microphone;
   a processor;
   an analog-to-digital converter electrically coupled to said microphone, said converter receiving an input signal in analog format based upon a user voice command and generating an output signal in digital format for instructing said processor to perform a control logic algorithm responsive to said input signal; and
   a memory including software instructions for causing said light-emitting assembly to perform the steps of biasing said motor assembly and activating said light-emitting source between on and off positions respectively.

3. The voice-activated lighting assembly of claim 1, wherein said motor assembly comprises:
   a signal interface circuit electrically and directly coupled to said converter;
   a motor electrically coupled to said power supply source;
   an anchor bracket monolithically formed with said strap and registered orthogonal thereto, said anchor bracket having a hollow cavity housing said motor and directing an electrical lead line from said light-emitting source to said power supply source;
   a pair of actuating arms directly and operably connected to said motor; and
   a deformably non-resilient shaft having opposed end portions directly conjoined to said actuating anchor bracket and monolithically formed with said actuating arms;
   wherein each said actuating arms is selectively adaptable along a linear path such that said shaft becomes adapted along at least two opposing planes.

4. The voice-activated lighting assembly of claim 1, wherein one said end portions of said shaft has an annular shape, said anchor bracket having an annular socket formed within a distal end portion of thereof, said one end portion of said shaft being rotatably seated within the annular socket of said anchor bracket.

5. The voice-activated lighting assembly of claim 1, wherein each said actuating arms comprises:
   a cylindrical housing provided with a centrally registered longitudinal axis traveling parallel to said anchor bracket, said housing having an axial bore formed therein;
   a magnetically-actuated piston telescopically intercalated within the bore; and
   a plurality of annular magnetic contacts concentrically positioned about the bore and said piston;
   wherein said annular magnetic contacts are selectively activated based upon said output signal generated by said converter in such a manner that said piston linearly travels along the bore when exposed to oscillating magnetic fields emitted by said magnetic contacts.

6. The voice-activated lighting assembly of claim 1, wherein said light-emitting assembly comprises:
   a housing having an open distal end portion;
   a transparent lens seated within said distal end portion; and
   a bulb centrally nested with said housing, said bulb being disposed proximal said transparent lens for directing light rays outwardly and away from said housing.

7. A voice-activated lighting assembly positional about a user's head, said lighting assembly comprising:
   a continuous and unitary strap adaptable to a variety of annular positions, said strap being suitably sized and shaped for being placed directly about the user's head in such a manner that said strap remains above a line of sight of the user;
   a light-emitting source distally spaced from said strap;
   a power supply source electrically coupled to said light-emitting assembly, said power supply source being rechargeable;

voice-activated means for biasing said light-emitting source between a variety of positions distally defined from said strap so that said light-emitting assembly can be adapted along an x-axis, y-axis and z-axis while a user's hands remain spaced from said lighting assembly; and a motor assembly directly and operably conjoined to said voice-activated means and said light-emitting assembly;

wherein said voice-activated means cooperates with said light-emitting source and said motor assembly during operating conditions, said voice-activated means being responsive to a user's voice commands in such a manner that the user can selectively operate said motor assembly and said light-emitting source from a remote location.

8. The voice-activated lighting assembly of claim 7, wherein said voice-activated means comprises:

a microphone;

a processor;

an analog-to-digital converter electrically coupled to said microphone, said converter receiving an input signal in analog format based upon a user voice command and generating an output signal in digital format for instructing said processor to perform a control logic algorithm responsive to said input signal; and a memory including software instructions for causing said light-emitting assembly to perform the steps of biasing said motor assembly and activating said light-emitting source between on and off positions respectively.

9. The voice-activated lighting assembly of claim 7, wherein said motor assembly comprises:

a signal interface circuit electrically and directly coupled to said converter;

a motor electrically coupled to said power supply source;

an anchor bracket monolithically formed with said strap and registered orthogonal thereto, said anchor bracket having a hollow cavity housing said motor and directing an electrical lead line from said light-emitting source to said power supply source;

a pair of actuating arms directly and operably connected to said motor; and a deformably non-resilient shaft having opposed end portions directly conjoined to said actuating anchor bracket and monolithically formed with said actuating arms;

wherein each said actuating arms is selectively adaptable along a linear path such that said shaft becomes adapted along at least two opposing planes.

10. The voice-activated lighting assembly of claim 7, wherein one said end portions of said shaft has an annular shape, said anchor bracket having an annular socket formed within a distal end portion of thereof, said one end portion of said shaft being rotatably seated within the annular socket of said anchor bracket.

11. The voice-activated lighting assembly of claim 7, wherein each said actuating arms comprises:

a cylindrical housing provided with a centrally registered longitudinal axis traveling parallel to said anchor bracket, said housing having an axial bore formed therein;

a magnetically-actuated piston telescopically intercalated within the bore; and a plurality of annular magnetic contacts concentrically positioned about the bore and said piston;

wherein said annular magnetic contacts are selectively activated based upon said output signal generated by said converter in such a manner that said piston linearly travels along the bore when exposed to oscillating magnetic fields emitted by said magnetic contacts.

12. The voice-activated lighting assembly of claim 7, wherein said light-emitting assembly comprises:

a housing having an open distal end portion;

a transparent lens seated within said distal end portion; and a bulb centrally nested with said housing, said bulb being disposed proximal said transparent lens for directing light rays outwardly and away from said housing.

13. A voice-activated lighting assembly positional about a user's head, said lighting assembly comprising:

a continuous and unitary strap adaptable to a variety of annular positions, said strap being suitably sized and shaped for being placed directly about the user's head in such a manner that said strap remains above a line of sight of the user;

a light-emitting source distally spaced from said strap;

a power supply source electrically coupled to said light-emitting assembly, said power supply source being rechargeable;

voice-activated means for biasing said light-emitting source between a variety of positions distally defined from said strap so that said light-emitting assembly can be adapted along an x-axis, y-axis and z-axis while a user's hands remain spaced from said lighting assembly; and a motor assembly directly and operably conjoined to said voice-activated means and said light-emitting assembly;

wherein said voice-activated means cooperates with said light-emitting source and said motor assembly during operating conditions, said voice operating means being power-operated, said voice-activated means being responsive to a user's voice commands in such a manner that the user can selectively operate said motor assembly and said light-emitting source from a remote location.

14. The voice-activated lighting assembly of claim 13, wherein said voice-activated means comprises:

a microphone;

a processor;

an analog-to-digital converter electrically coupled to said microphone, said converter receiving an input signal in analog format based upon a user voice command and generating an output signal in digital format for instructing said processor to perform a control logic algorithm responsive to said input signal; and a memory including software instructions for causing said light-emitting assembly to perform the steps of biasing said motor assembly and activating said light-emitting source between on and off positions respectively.

15. The voice-activated lighting assembly of claim 13, wherein said motor assembly comprises:

a signal interface circuit electrically and directly coupled to said converter;

a motor electrically coupled to said power supply source;

an anchor bracket monolithically formed with said strap and registered orthogonal thereto, said anchor bracket having a hollow cavity housing said motor and directing an electrical lead line from said light-emitting source to said power supply source;

a pair of actuating arms directly and operably connected to said motor; and a deformably non-resilient shaft having opposed end portions directly conjoined to said actuating anchor bracket and monolithically formed with said actuating arms;

wherein each said actuating arms is selectively adaptable along a linear path such that said shaft becomes adapted along at least two opposing planes.

16. The voice-activated lighting assembly of claim 13, wherein one said end portions of said shaft has an annular shape, said anchor bracket having an annular socket formed within a distal end portion of thereof, said one end portion of said shaft being rotatably seated within the annular socket of said anchor bracket.

17. The voice-activated lighting assembly of claim 13, wherein each said actuating arms comprises:

a cylindrical housing provided with a centrally registered longitudinal axis traveling parallel to said anchor bracket, said housing having an axial bore formed therein;

a magnetically-actuated piston telescopically intercalated within the bore; and a plurality of annular magnetic contacts concentrically positioned about the bore and said piston;

wherein said annular magnetic contacts are selectively activated based upon said output signal generated by said converter in such a manner that said piston linearly travels along the bore when exposed to oscillating magnetic fields emitted by said magnetic contacts.

18. The voice-activated lighting assembly of claim 13, wherein said light-emitting assembly comprises:

a housing having an open distal end portion;

a transparent lens seated within said distal end portion; and a bulb centrally nested with said housing, said bulb being disposed proximal said transparent lens for directing light rays outwardly and away from said housing.

\* \* \* \* \*